(12) United States Patent
Madabhushi et al.

(10) Patent No.: US 9,984,462 B2
(45) Date of Patent: *May 29, 2018

(54) DISEASE CHARACTERIZATION FROM FUSED PATHOLOGY AND RADIOLOGY DATA

(71) Applicant: Case Western Reserve University, Cleveland, OH (US)

(72) Inventors: Anant Madabhushi, Shaker Heights, OH (US); Mirabela Rusu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/705,904

(22) Filed: Sep. 15, 2017

(65) Prior Publication Data
US 2018/0012356 A1 Jan. 11, 2018

Related U.S. Application Data

(63) Continuation-in-part of application No. 14/964,665, filed on Dec. 10, 2015, now Pat. No. 9,767,555.
(Continued)

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *G06K 9/4604* (2013.01);
(Continued)

(58) Field of Classification Search
USPC ......................................................... 382/128
See application file for complete search history.

(56) References Cited

U.S. PATENT DOCUMENTS 5,625,705 A * 4/1997 Recht ................... G06K 9/0014
382/128
8,135,202 B2 * 3/2012 Cosatto et al. .... G06K 9/00147
382/133
(Continued)

OTHER PUBLICATIONS

Notice of Allowance dated May 23, 2017 for U.S. Appl. No. 14/964,665.
(Continued)

*Primary Examiner* — Gregory F Cunningham
(74) *Attorney, Agent, or Firm* — Eschweiler & Potashnik, LLC

(57) ABSTRACT

Methods and apparatus distinguish invasive adenocarcinoma (IA) from in situ adenocarcinoma (AIS). One example apparatus includes a set of circuits, and a data store that stores three dimensional (3D) radiological images of tissue demonstrating IA or AIS. The set of circuits includes a classification circuit that generates an invasiveness classification for a diagnostic 3D radiological image, a training circuit that trains the classification circuit to identify a texture feature associated with IA, an image acquisition circuit that acquires a diagnostic 3D radiological image of a region of tissue demonstrating cancerous pathology and that provides the diagnostic 3D radiological image to the classification circuit, and a prediction circuit that generates an invasiveness score based on the diagnostic 3D radiological image and the invasiveness classification. The training circuit trains the classification circuit using a set of 3D histological reconstructions combined with the set of 3D radiological images.

26 Claims, 8 Drawing Sheets

Related U.S. Application Data

(60) Provisional application No. 62/099,634, filed on Jan. 5, 2015.

(51) Int. Cl.
  *G06T 7/11* (2017.01)
  *G06T 11/00* (2006.01)
  *G06K 9/62* (2006.01)
  *A61B 6/03* (2006.01)
  *G06K 9/46* (2006.01)

(52) U.S. Cl.
  CPC .............. *G06K 9/6267* (2013.01); *G06T 7/11* (2017.01); *G06T 11/006* (2013.01); *G06T 2207/10081* (2013.01); *G06T 2207/30024* (2013.01); *G06T 2207/30096* (2013.01)

(56) References Cited

U.S. PATENT DOCUMENTS

| | | | |
|---|---|---|---|
| 2012/0189176 A1* | 7/2012 | Giger | G06K 9/6253 382/128 |
| 2016/0196648 A1 | 7/2016 | Madabhushi et al. | |
| 2017/0103525 A1 | 4/2017 | Hu et al. | |

OTHER PUBLICATIONS

Rusu, et al. "Co-registration of Pre-Operative CT with Ex Vivo Surgically Excised Ground Glass Nodules to Define Spatial Extent of Invasive Adenocarcinoma on in Vivo Imaging: A Proof-of-Concept Study." Eur Radiol (2017) 27:4209-4217. Published Apr. 6, 2017.

\* cited by examiner

DISEASE CHARACTERIZATION FROM FUSED PATHOLOGY AND RADIOLOGY DATA

CROSS REFERENCE TO RELATED APPLICATIONS

This application is a Continuation-in-Part of U.S. application Ser. No. 14/964,665 filed on Dec. 10, 2015, which claims priority to U.S. Provisional Application No. 62/099,634 filed on Jan. 5, 2015. The contents of the above-referenced matters are hereby incorporated by reference in their entirety.

BACKGROUND

Invasive and in situ or non-invasive components may co-exist within the same pulmonary adenocarcinoma nodule. This may result in a heterogeneous ground glass nodule (GGN) represented in a computed tomography (CT) image. Conventional approaches are unable to distinguish GGNs exhibiting minimal invasion from GGNs exhibiting frank invasion on CT. Conventional approaches rely on histopathology to definitively identify the extent of invasive adenocarcinoma (IA) from in situ or non-invasive adenocarcinoma (AIS) within a GGN.

Guidelines for managing GGNs detected in CT imagery have been proposed but are not widely implemented. These guidelines consider the size of the GGN and the size of the solid component as represented in the CT imagery. Conventional approaches may examine the relationship between the solid component size and cancer prognosis. However, conventional approaches do not map IA detected by histological examination to data provided by CT imaging.

Registering ex vivo histology slices to pulmonary CT imagery is challenging. Pulmonary tissue, or other cancerous tissue, is soft and collapses during histology preparation, causing elastic deformations and ripping of the tissue. Correspondences between histology slices and CT imagery are also difficult to identify because histology specimens are frequently obliquely sectioned without consideration of the CT reconstruction. Furthermore, in a clinical setting, only a relatively small number of histology slices may be available from a GGN, and these slices may have been frozen or prepared after fixation, causing further deformities.

Some conventional approaches have attempted to reconstruct thinly sliced lung adenocarcinoma histology slices into three dimensional (3D) models, but these 3D reconstructions are not registered to CT imagery. At least 25% of nodules identified on baseline CT imagery are GGN nodules. GGNs that persist on follow-up scans often represent early cancers that, if resected, have a five year disease free survival range of between 67% and 100%, depending on the extent of IA in the GGN. Thus, a more accurate way to distinguish IA from AIS in GGNs detected in CT imagery would facilitate improved patient outcomes and reduce un-needed invasive procedures.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example methods and apparatus distinguish invasive adenocarcinoma (IA) from in situ or non-invasive adenocarcinoma (AIS) represented in a three dimensional (3D) computed tomography (CT) image of a region of tissue demonstrating cancerous pathology. The 3D CT image may include representations of ground glass nodules (GGN). Example methods and apparatus perform a 3D histological reconstruction of histological slices of a GGN and register the 3D histological reconstruction with a 3D CT image of the GGN, thus combining or "fusing" the 3D histological reconstruction with the 3D CT image. Example methods and apparatus map regions of IA detected in the 3D histology reconstruction to the 3D CT image and extract texture or shape features associated with IA from the 3D CT image. A classifier may be trained to detect computer extracted textural or shape features associated with IA in a 3D CT image.

Example apparatus and methods use histologic reconstruction and deformable co-registration to map the extent of IA represented in a 3D histopathology reconstruction of a set of histological slices of a GGN onto a 3D CT image of the GGN. The 3D histological reconstruction is combined with the 3D CT imagery using elastic registration techniques. Machine learning techniques may be used to train a classifier to distinguish IA from AIS using the combined 3D histology-3D CT data. The classifier may distinguish IA from AIS by identifying texture or shape features associated with IA in the 3D CT imagery. The classifier may use, for example, support vector machine (SVM) regression or other machine learning techniques. Example methods and apparatus facilitate assessment of the presence of significant invasion. Significant invasion may be defined as invasion greater than five millimeters (mm).

Figure 6:
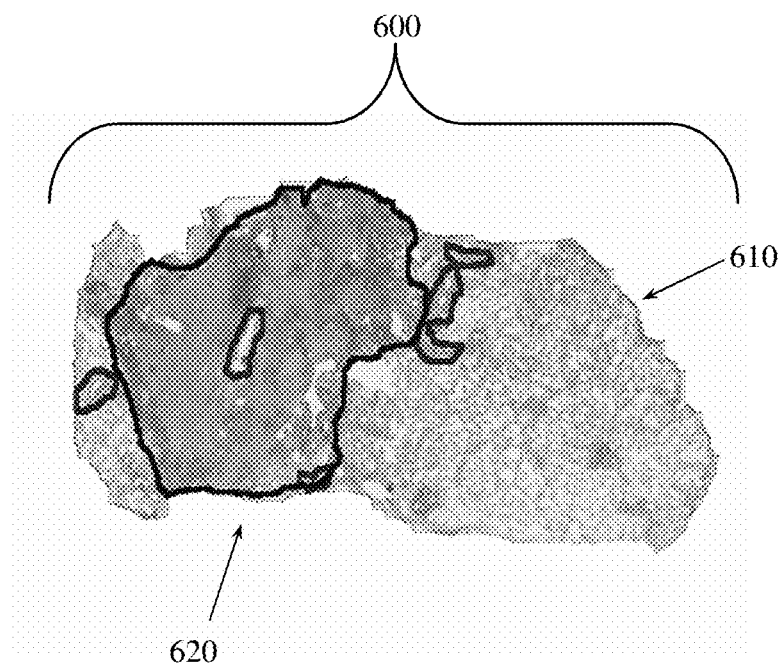
FIG. 6 illustrates a histology slice of a region of tissue demonstrating IA and AIS.

In one embodiment, 3D CT imagery and histology slices of resected GGNs with significant (n=9) and minimal or no (n=5) invasion are examined. Following high-resolution scanning of histology slides of a GGN, invasive and in situ components are outlined automatically or by an expert pathologist. FIG. 6 is an illustration of a histological slice 600 of a GGN. IA tissue 620 is outlined and distinguished from non-invasive tissue 610. The outlines may be mapped onto CT images of the region of tissue through co-registration of the histology with CT images.

Figure 7:
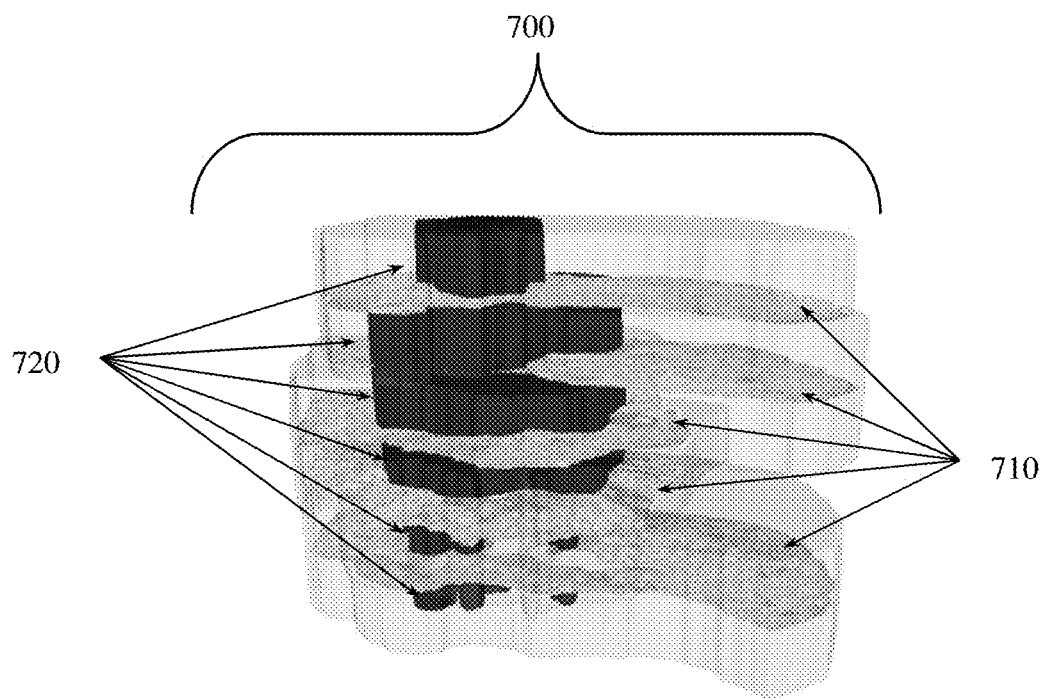
FIG. 7 illustrates a 3D histology reconstruction of a set of histology slices demonstrating IA and AIS.

Example methods and apparatus perform a 3D histological reconstruction of a region of tissue demonstrating IA or AIS using the histology slices. In one embodiment, the 3D histological reconstruction uses a combined natural gradient and group-wise alignment based approach. FIG. 7 is an illustration of an example 3D histological reconstruction 700. A set of histology slices 710 in which IA and AIS tissue have been annotated are registered. A member of the set of histology slices 710 may have a slice thickness (e.g. 5 mm). IA tissue 720 is extrapolated into the 3D histological reconstruction from the annotation of the individual slices. While the histology slices may be approximately two dimensional, the invasive component extends continuously in three dimensions in the actual GGN. Thus, example methods and apparatus facilitate extending the annotated IA or AIS components from the histology slices into the 3D histology reconstruction. The 3D histology reconstruction may be generated using a slice spacing (e.g. 3 mm, 4 mm) that is less than the slice thickness. Using a slice spacing that is less than the slice thickness facilitates a more accurate registration by accounting for histology slice shrinkage that may occur during histology sample fixation.

Figure 8:
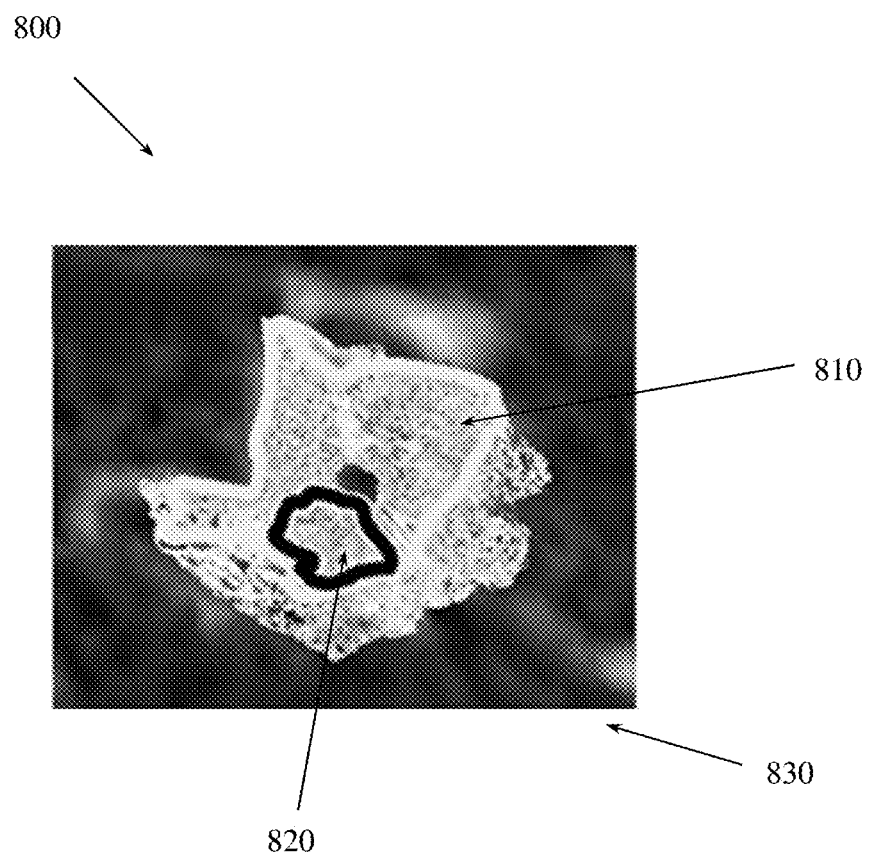
FIG. 8 illustrates a member of a set of 3D histology reconstructions of a region of tissue registered with a slice from a 3D CT image of the region of tissue.

Following 3D reconstruction of the histological nodule, the 3D histologic reconstruction is registered to the nodule segmented on CT. FIG. 8 is an illustration of a fused histological-CT image 800. Fused histological-CT image 800 represents a 3D histological reconstruction slice combined with a CT image of the same region of tissue. IA tissue 820 and non-invasive tissue 810 are registered with the CT image 830 of the same region of tissue. In one embodiment, affine and elastic registration facilitates mapping the extent of invasion from ex vivo pathology represented by IA tissue 820 and non-invasive tissue 810 onto corresponding CT imagery represented by CT image 830. Affine and elastic registration facilitates correcting deformations suffered by the tissue during excision and histology preparation. Recovering non-linear deformations between the template and target images facilitates registering the 3D histological reconstruction with the CT imagery.

In some situations, histology slices may not be taken in the same plane that CT images are taken. Example methods and apparatus may employ an interactive CT nodule sectioning to identify a CT tumor plane that matches the plane of the histology slice. The matching may be performed by visually matching anatomic landmarks that are represented on both the histology slice and the CT image. An anatomic landmark may be, for example, a blood vessel or other structure discernible on both the histology slice and the CT image. The histology slice and the corresponding CT slices are then aligned using elastic registration approaches.

In one embodiment, a histologic section from an excised lung nodule is registered with a corresponding pre-operative CT image. A region of invasion determined from the histology may then be mapped onto the CT image. The histologic sectioning may be performed in a direction oblique to the CT axial, coronal, or sagittal views. Using anatomic landmarks, including pleura or blood vessels, the cutting plane may be identified and the CT scan may be resampled in that plane. The histology slices may be automatically aligned to their CT oblique correspondent.

In one embodiment, CT-derived features are extracted to identify and distinguish IA from AIS. CT-derived features may include intensity statistics, Haralick features, Gabor features, or other textural features that facilitate characterizing the textural appearance of the nodule and identifying those features that distinguish IA from in situ disease. The textural features may be extracted based on intensity alone without considering shape, or the textural features may be extracted with consideration of shape. In another embodiment, shape features may also be extracted and used to distinguish invasion from in situ disease.

Example apparatus and methods perform a more accurate registration of histology and CT than conventional approaches. Example apparatus and methods thus facilitate mapping the invasive and in situ components from the 3D histology reconstruction onto 3D CT. The accuracy of the registration may be assessed by measuring the deviation of anatomic landmarks including, for example, blood vessels, between the histology and CT imagery. Example methods and apparatus achieve a registration accuracy of at least 66%, which is a significant improvement over conventional approaches.

Upon mapping IA or AIS from the 3D histological reconstruction to the 3D CT imagery, example methods and apparatus may resample the 3D CT imagery to have consistent voxel sizes. In one embodiment, a consistent voxel size of 0.5 $mm^3$ is employed. In another embodiment, other voxel sizes may be employed.

Example methods and apparatus may also be applied to other types of cancer, including breast cancer. Example apparatus and methods may use images provided by DCE (dynamic contrast enhanced) MRI (magnetic resonance imaging) as well as or in addition to CT imagery. Due to the size of excised breast cancer samples, a lumpectomy specimen may be sectioned into hemispheres instead of the planar histological slices employed with GGNs. In one embodiment, digitized images are digitally stitched to create a pseudo-whole mount histology section using a HistoStitcher. The digital 3D histology lumpectomy specimen is then reconstructed utilizing a group-wise registration method. The 3D reconstruction of the histology facilitates true 3D to 3D registration between the histology and DCE-MRI. An affine transform followed by a selective deformable registration is applied, allowing the mapping of the residual cancer extent from the histology onto MRI.

By fusing histology with CT and image analytics to train classifiers to distinguish IA from AIS, example methods and apparatus facilitate the early detection of invasive adenocarcinoma on pre-operative CT. Example methods and apparatus thus produce the concrete, real-world technical effect of increasing the accuracy of invasion characterization. Additionally, example apparatus and methods increase the probability that at-risk patients receive timely treatment tailored to the particular pathology they exhibit. Example methods and apparatus may also reduce the number of invasive procedures needed to accurately predict IA in patients. The additional technical effect of reducing the expenditure of resources and time on patients who are less likely to suffer IA or disease progression is also achieved. Example methods and apparatus thus improve on conventional methods in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
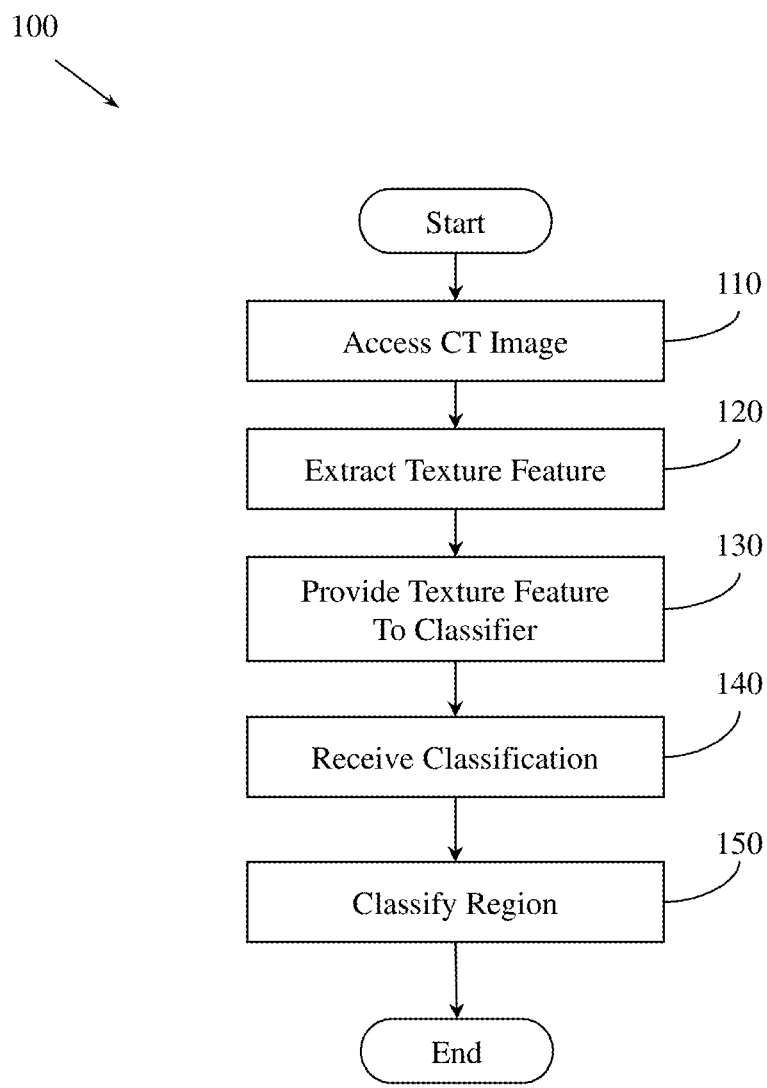
FIG. 1 illustrates an example method for distinguishing invasive adenocarcinoma (IA) from non-invasive adenocarcinoma (AIS).

FIG. 1 illustrates an example computerized method 100 for distinguishing IA from AIS. Method 100 includes, at 110, accessing a CT image of a region of tissue demonstrating cancerous pathology. Accessing the CT image may include accessing a CT image of a region of lung tissue. The CT image may include a texture feature or a shape feature. The region of tissue represented in the CT image may include a GGN. The CT image may be stored, for example, in a computer memory or may be provided across a computer network. In one embodiment, the CT image has an image size of 512 by 512 pixels. The CT image may have an in-plane resolution of 0.57 mm to 0.87 mm. A distance between a first member of a set of CT images and a second, different member of the set of CT images may be from 1 mm to 5 mm. In another embodiment, other images sizes, in-plane resolutions, distances between CT images, or imaging techniques may be employed.

Method 100 also includes, at 120, extracting a set of texture features from the CT image. The set of texture features may include intensity statistics, Haralick features, Gabor features, or other textural features used to characterize the textural appearance of the GGN represented in the CT image. The set of texture features may be used to identify features that distinguish IA from in situ disease. In another embodiment, shape features may also be extracted and used to distinguish IA from in situ disease.

Method 100 also includes, at 130, providing the set of texture features to an automated IA classifier. Method 100 also includes, at 140, receiving, from the IA classifier, a classification of the set of texture features. In one embodiment, the IA classifier is trained on a set of composite images. The composite images are formed from a set of 3D histology reconstructions of a region of tissue demonstrating IA or AIS combined with a set of 3D CT images of the region of tissue demonstrating IA or IAS.

Method 100 also includes, at 150, classifying the region of tissue as IA or AIS. Method 100 may classify the region of tissue based, at least in part, on the set of texture features and the classification. In one embodiment, method 100 may classify the region of tissue based on a shape feature extracted from the CT image.

Example methods and apparatus facilitate applying a more appropriately determined treatment based on the classification of IA within the area of tissue under investigation. Using a more appropriately determined and applied treatment may lead to less therapeutics being required for a patient or may lead to avoiding or delaying a biopsy, a resection, or other invasive procedure. When regions of cancerous tissue, including the lung captured in CT images, are more quickly and more accurately classified as likely or unlikely to experience IA, patients with poorer prognoses may receive a higher proportion of scarce resources (e.g., therapeutics, physician time and attention, hospital beds). Patients with better prognoses may thus be spared unnecessary treatment, which in turn spares unnecessary expenditures and resource consumption. Example methods and apparatus therefore have the real-world, quantifiable effects of improving patient outcomes and reducing resource expenditure.

While FIG. 1 illustrates various actions occurring in serial, it is to be appreciated that various actions illustrated in FIG. 1 could occur substantially in parallel. By way of illustration, a first process could access a CT image of a region of tissue demonstrating cancerous pathology, a second process could extract texture features from the CT image, and a third process could classify the region as IA or AIS. While three processes are described, it is to be appreciated that a greater or lesser number of processes could be employed and that lightweight processes, regular processes, threads, and other approaches could be employed.

Figure 2:
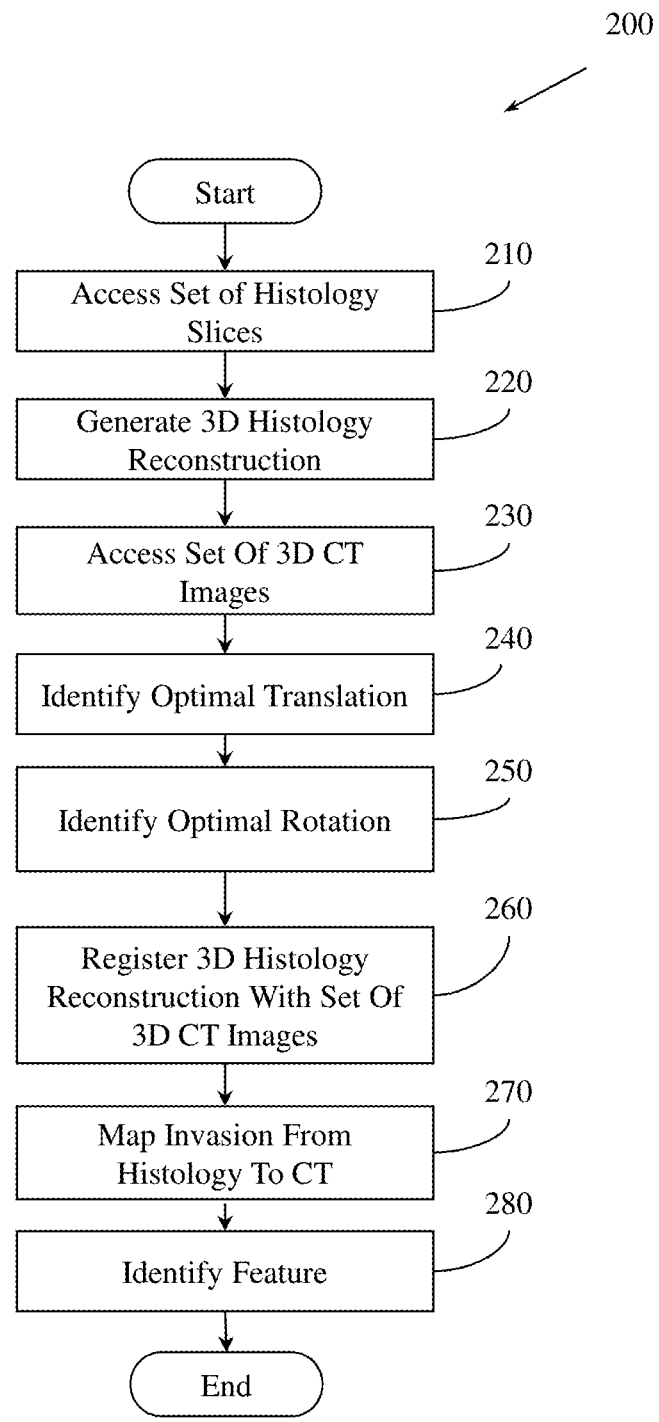
FIG. 2 illustrates an example method for distinguishing IA from AIS.

FIG. 2 illustrates a method 200 for combining a set of 3D histology reconstructions with a set of 3D CT images. Method 200 may be performed independently of method 100 or may be performed as an additional action during the performance of method 100. Method 200 includes, at 210, accessing a set of histology slices of a region of tissue demonstrating cancerous pathology. A member of the set of histology slices includes an invasive component and a non-invasive component. The invasive component may be invasive adenocarcinoma, while the non-invasive component may be in situ adenocarcinoma. The invasive component or the non-invasive component may be automatically annotated, or may be annotated by an expert pathologist.

In one embodiment of method 200, accessing the set of histology slices may further include preprocessing the set of histology slices. In one embodiment, preprocessing the set of histology slices includes down-sampling a member of the set of histology slices. For example, method 200 may preprocess the set of histology slices by down-sampling the member of the set of histology slices to a pixel resolution of 39 µm in the X-Y plane. In another embodiment, the member of the set of histology slices may be down-sampled to another, different pixel resolution. In one embodiment, preprocessing the set of histology slices includes rotating members of the set of histology slices to achieve a threshold level of gross alignment relative to each other. The threshold level of gross alignment may be based on available computational resources, a time available for preprocessing, a desired level of alignment, or other factors. In another embodiment, other, different preprocessing techniques may be employed.

Method 200 also includes, at 220, generating a 3D histology reconstruction of the set of histology slices. Generating the 3D histology reconstruction of the set of histology slices may include performing a group-wise registration of at least two members of the set of histology slices. Method 200 may determine a rotation or a translation with which to rotate or translate a first histology slice with respect to a second, different histology slice.

In one embodiment, the group-wise registration may include aligning members of the set of histology slices using a rigid transformation. For example, a rigid transformation may include an in-plane 2D translation or a rotation. In one embodiment, the group-wise registration may employ an iterative registration approach. For example, a first member of the set of histology slices may be aligned relative to a second, different member of the set of histology slices using mutual information to assess their spatial alignment. Mutual information (MI) of two random variables is a measure of the mutual dependence between the two variables. MI may quantify the amount of information obtained about one random variable, through the other random variable. The amount of information may be quantified in units, including shannons or bits. A third, different member of the set of histology slices may then be aligned relative to the first and second members of the set of histology slices using, in one embodiment, a weighted average of mutual information. This process may then be iterated further for a fourth member of the set of histology slices or a fifth member of the set of histology slices for a nodule with N=4 or N=5 slices. In another embodiment, other numbers of slices may be iteratively registered.

A member of the set of histology slices may have a thickness. The member of the set of histology slices may have been acquired having an original thickness. However, tissue shrinkage may occur during histology sample fixation. Thus, while an institution (e.g. hospital, university, pathology laboratory) may commonly perform tissue sectioning for lung nodules with a 4 mm to 5 mm slice spacing, the histology slices may shrink. Performing a 3D histology reconstruction using a slice-spacing that corresponds to the original slice thickness may therefore lead to sub-optimal registration. Example embodiments may generate the 3D histology reconstruction of the set of histology slices using a slice spacing that is less than the original slice thickness of the member of the set of histology slices. For example, a member of the set of histology slices may have been acquired using a 5 mm slice thickness. The member of the set of histology slices may have experienced tissue shrinkage during histology sample fixation. Thus, in one embodiment, generating the 3D histology reconstruction of the set of histology slices includes generating the 3D histology reconstruction of the set of histology slices using a slice spacing that is less than the original thickness. In one embodiment, generating the 3D histology reconstruction of the set of histology slices is performed using a 3 mm slice spacing. In another embodiment, generating the 3D histology reconstruction of the set of histology slices is performed using a 4 mm slice spacing. In another embodiment, generating the 3D histology reconstruction of the set of histology slices is performed using a slice spacing that ranges from 3 mm to 4 mm.

Method 200 also includes, at 230, accessing a set of 3D radiological images of the region of tissue. A member of the set of 3D radiological images includes a texture feature or a shape feature. In one embodiment, example methods and apparatus may extract at least 189 texture features from the set of 3D radiological images. In one embodiment, a member of the set of 3D radiological images is a CT image. In another embodiment, a member of the set of 3D radiological images may be an MR image.

In one embodiment, the 3D histology reconstruction may be refined using a local search constrained by the set of 3D radiological images. Refining the 3D histology reconstruction constrained by the set of 3D radiological images involves considering the GGN segmented by the CT imagery while adjusting the rotation or translation of the histology slices within the 3D histology reconstruction.

Method 200 also includes, at 240, identifying an optimal translation of the set of 3D radiological images relative to the 3D histology reconstruction. An optimal translation is a translation that matches or registers the 3D histology reconstruction to the 3D radiological images to within a threshold accuracy. Example methods and apparatus register the 3D histology reconstruction to the 3D radiological images to within at least 66% accuracy. In one embodiment, the optimal translation is an affine translation, or a deformable translation. Method 200 also includes, at 250, identifying an optimal rotation of the set of 3D radiological images relative to the 3D histology reconstruction.

In one embodiment, a global search is employed to identify the optimal rotation of the set of 3D radiological images relative to the 3D histology reconstruction. In this embodiment, a grid-like search is employed to achieve alignment between the moving volume and the fixed volume. In this example the 3D radiological images on CT are the moving volume, and the fixed volume is the 3D histology reconstruction. In one embodiment, the grid-like search may be implemented using an intensity-based medical image registration approach. Identifying the optimal rotation may also include using a FullSearchSpace optimization. A full search space optimization includes identifying the optimal set of parameters for rotation across every possible combination of variables (i.e. spanning the entire search space).

Method 200 also includes, at 260, registering the 3D histology reconstruction with the set of 3D radiological images. The 3D histology reconstruction and the set of 3D radiological images may be registered based, at least in part, on the optimal translation or the optimal rotation.

Method 200 also includes, at 270, mapping the extent of cancerous invasion from the 3D histology reconstruction onto the set of 3D radiological images. Mapping the extent of cancerous invasion from the 3D histology reconstruction onto the set of 3D radiological images includes using an inverse of the optimized affine translation or an inverse of the optimized deformable translation.

Method 200 also includes, at 280, identifying, based, at least in part on the mapping, a texture feature or a shape feature associated with an invasive component. The texture feature associated with the invasive component may be a first-order statistic. The first-order statistic may be the top-ranked feature according to the Bhattacharyya distance. In one embodiment, the first-order statistic may be computed from a mean of CT intensity of a sliding 3×3×3 voxel window obtained from a member of the set of 3D CT images.

Figure 3:
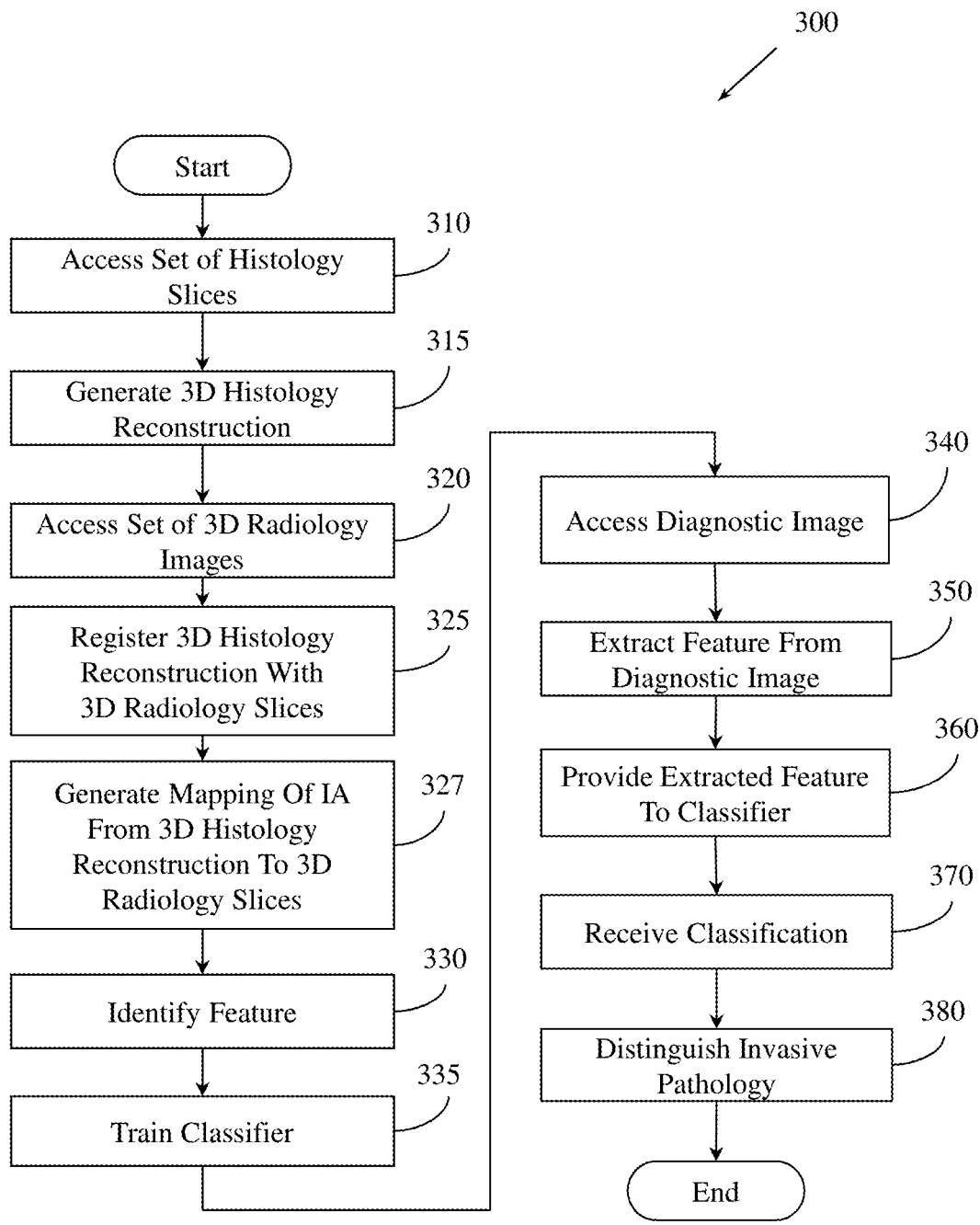
FIG. 3 illustrates an example method for distinguishing invasive carcinoma from non-invasive carcinoma.

FIG. 3 illustrates a method 300 for distinguishing invasive cancerous pathology from non-invasive pathology. Method 300 includes, at 310, accessing a set of histology slices of a region of tissue demonstrating invasive cancerous pathology and non-invasive cancerous pathology. In one embodiment, the slices are stained with hematoxylin and eosin (H&E) and scanned at a 20× magnification with a pixel size of 0.25 µm. In another embodiment, other types of stain, scanning magnification, or pixel sizes may be employed.

Method 300 also includes, at 315, generating a 3D histology reconstruction of the set of histology slices. Generating the 3D histology reconstruction may include performing a group-wise registration of at least two members of the set of histology slices.

Method 300 also includes, at 320, accessing a set of 3D radiological images of the region of tissue. A member of the set of 3D radiological images includes a texture feature or a shape feature. In one embodiment, a member of the set of 3D radiological images is a CT image. In another embodiment, a member of the set of 3D radiological images is a DCE MRI image.

Method 300 also includes, at 325, registering the 3D histology reconstruction with the set of 3D radiological images. The 3D histology reconstruction and the set of 3D radiological images may be registered based, at least in part, on an optimal translation or an optimal rotation described in connection with actions 240-260 (FIG. 2). Registering the 3D histology reconstruction with the set of 3D radiological images may include performing an affine registration or an elastic registration.

Method 300 also includes, at 327, generating a mapping of invasive cancerous pathology from the 3D histology reconstruction onto the set of 3D radiological images based. In one embodiment, the mapping is based, at least in part, on the registration.

Method 300 also includes, at 330, identifying, in a member of the set of 3D radiological images, a texture feature or a shape feature associated with invasive cancerous pathology. The identification of the texture feature or shape feature may be based, at least in part, on the mapping.

Method 300 also includes, at 335, training a classifier to distinguish invasive cancerous pathology from non-invasive cancerous pathology. In one embodiment, the classifier may be trained to distinguish IA from AIS, based, at least in part, on the mapping, a texture feature, or a shape feature. Training a classifier may include training a support vector machine (SVM) using the "fused" histology-CT data as a set of training examples. The SVM may be trained to classify a region of tissue based on texture features associated with IA and to classify the region of tissue based on texture features associated with AIS. Example methods and apparatus may extract features from the "fused" histology-CT data and apply SVM regression to characterize the level of invasion. In one embodiment, SVM regression may be used to determine an IA score. For example, the SVM may learn to classify an image based on a texture feature that was extracted from the 3D radiological image that matches a previously learned texture feature to within a threshold. Other machine learning approaches may also be employed, including clustering, decision trees, or artificial neural networks.

In one embodiment, method 300 may include additional actions 340-380. In this embodiment method 300 includes, at 340 accessing a diagnostic 3D radiological image of a region of tissue demonstrating cancerous pathology. The diagnostic 3D radiological image may be a CT image or a DCE MRI image.

Method 300 also includes, at 350, extracting a texture feature or a shape feature from the diagnostic 3D radiological image. Extracting a texture feature or shape feature may be performed similarly to the extraction described in connection with action 120 (FIG. 1). The texture feature may be an intensity statistic, a Haralick feature, a Gabor feature, or other textural feature.

Method 300 also includes, at 360, providing the extracted texture feature or the extracted shape feature to the classifier. Providing the extracted texture feature of the extracted shape feature may be performed similarly to action 130 (FIG. 1). The extracted texture feature may be provided to a classifier across a network, to a classifier in a cloud service, or to a logic in an IA distinguishing apparatus.

Method 300 also includes, at 370, receiving, from the classifier, a first classification. The first classification may be based, at least in part, on the extracted texture feature or the extracted shape feature.

Method 300 also includes, at 380, distinguishing invasive cancerous pathology represented in the diagnostic 3D radiological image from non-invasive cancerous pathology represented in the diagnostic 3D image. Method 300 may distinguish IA from AIS represented in the diagnostic 3D radiological image based, at least in part, on the first classification and the texture feature or the shape feature.

In one example, a method may be implemented as computer executable instructions. Thus, in one example, a computer-readable storage device may store computer executable instructions that if executed by a machine (e.g., computer) cause the machine to perform methods described or claimed herein including method 100, method 200, and method 300. While executable instructions associated with the listed methods are described as being stored on a computer-readable storage device, it is to be appreciated that executable instructions associated with other example methods described or claimed herein may also be stored on a computer-readable storage device. In different embodiments, the example methods described herein may be triggered in different ways. In one embodiment, a method may be triggered manually by a user. In another example, a method may be triggered automatically.

Figure 4:
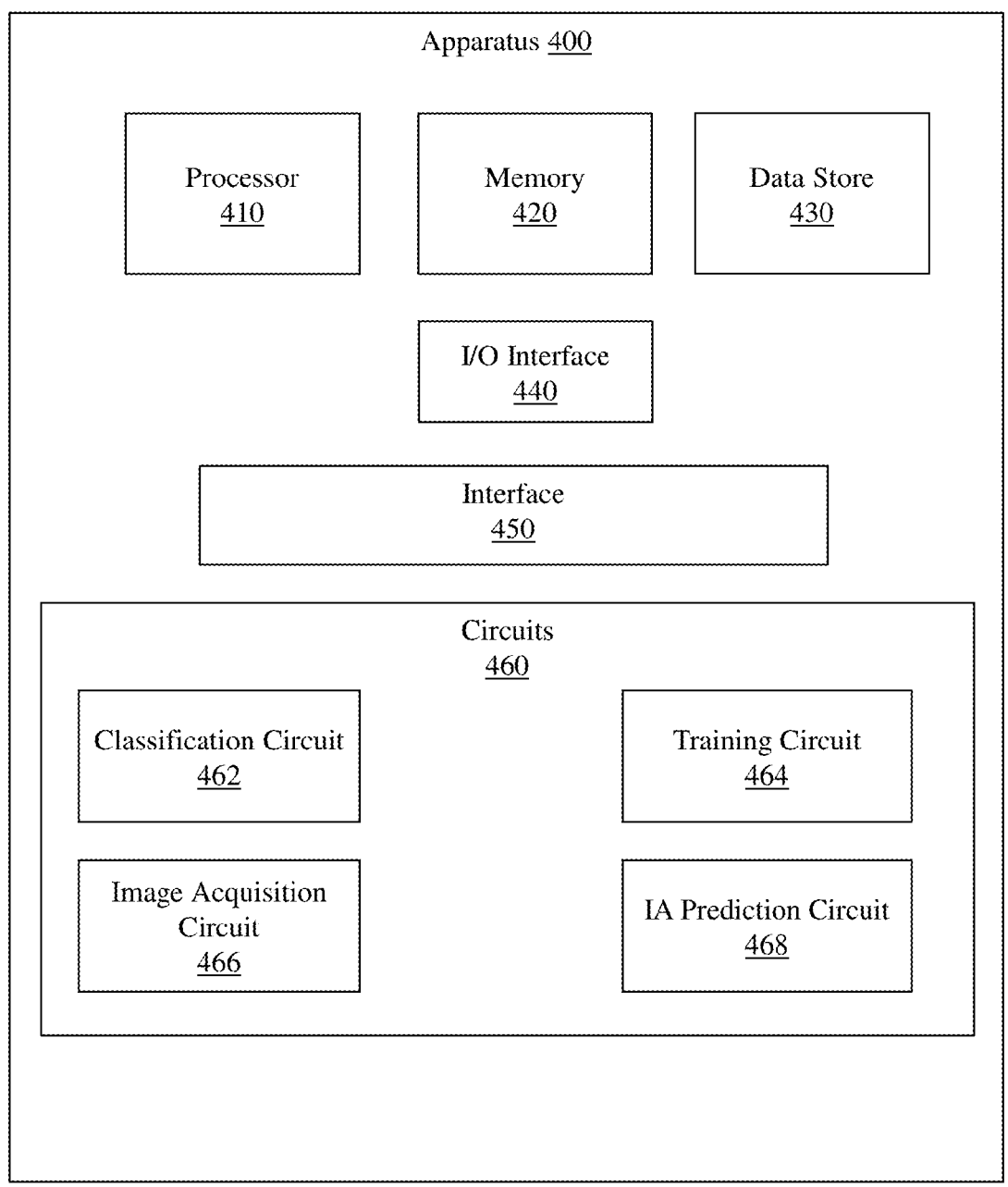
FIG. 4 illustrates an example apparatus for distinguishing IA from AIS.

FIG. 4 illustrates an example apparatus 400. Apparatus may be used for distinguishing invasive tissue from non-invasive tissue in a region of tissue demonstrating cancerous pathology. In one embodiment, apparatus 400 distinguishes IA from AIS in a region of tissue demonstrating cancerous pathology. Apparatus 400 includes a processor 410, a memory 420, a data store 430, an input/output (I/O) interface 440, a set of circuits 460, and an interface 450 that connects the processor 410, the memory 420, the data store 430, the I/O interface 440, and the set of circuits 460. Data store 430 stores a set of 3D radiological images of tissue demonstrating invasive or non-invasive pathology. In one embodiment, data store 430 stores a set of 3D radiological images of tissue demonstrating IA or AIS. A member of the set of 3D radiological images includes a texture feature or a shape feature.

The set of circuits 460 includes a classification circuit 462, a training circuit 464, an image acquisition circuit 466, and an IA prediction v 468. In one embodiment, the functionality associated with the set of circuits 460 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of circuits 460 are implemented as ASICs or SOCs.

In one embodiment, classification circuit 462 generates the invasiveness classification by distinguishing IA from AIS represented in the diagnostic 3D radiological image based, at least in part, on a texture feature extracted from the diagnostic 3D radiological image or a shape feature extracted from the diagnostic 3D radiological image. In another embodiment, classification circuit 462 may distinguish invasion from non-invasion associated with other types of cancer, including breast cancer.

In one embodiment, training circuit 464 trains the classification circuit 462 using a 3D histology reconstruction of a region of tissue demonstrating IA or AIS combined with the set of 3D radiological images of the region of tissue. Training circuit 464 combines the 3D histology reconstruction with the set of 3D radiological images by accessing a set of histology slices of a region of tissue demonstrating IA or AIS. Training circuit 464 may then generate a 3D histology reconstruction of the set of histology slices. Training circuit 464 may then access the set of 3D radiological images of the region of tissue. Training circuit 464 may then register the 3D histology reconstruction with the set of 3D radiological images. Training circuit 464 may generate a mapping of IA from the 3D histology reconstruction onto the set of 3D radiological images, and identify, in a member of the set of 3D radiological images, a texture feature or a shape feature associated with IA based, at least in part, on the mapping.

In one embodiment, generating the 3D histology reconstruction of the set of histology slices includes iteratively registering a first member of the set of histology slices relative to a second, different member of the set of histology slices. Generating the 3D histology reconstruction may further include iteratively registering at least a third, different member of the set of histology slices relative to the first and second members of the set of histology slices.

In one embodiment, registering the 3D histology reconstruction with the set of 3D radiological images includes identifying an optimal translation of the set of 3D radiological images relative to the 3D histology reconstruction. Registering the 3D histology reconstruction with the set of 3D radiological images further includes identifying an optimal rotation of the set of 3D radiological images relative to the 3D histology reconstruction. Identifying the optimal rotation may include using a grid-like search to achieve alignment between the set of 3D radiological images and the 3D histology reconstruction. The grid-like search may be based on an intensity-based medical image registration approach, or on a full search space optimization. Training circuit 464 may, in this embodiment, register the 3D histology reconstruction with the set of 3D radiological images based, at least in part, on the optimal rotation and the optimal translation.

In one embodiment, the set of circuits 460 also includes a display circuit. The display circuit may control a computer assisted diagnostic (CADx) system to display the invasiveness classification, the diagnostic 3D radiological image, the texture feature, the shape feature, or the 3D histology reconstruction combined with the set of 3D radiological images. By displaying the diagnostic 3D radiological image along with the invasiveness classification, the texture feature, the shape feature, or the 3D histology reconstruction combined with the set of 3D radiological images, example apparatus provide a timely and intuitive way for a human pathologist to more accurately classify pathologies demonstrated by a patient, thus improving on conventional approaches to characterizing cancerous invasion, or predicting cancer recurrence and disease progression.

Figure 5:
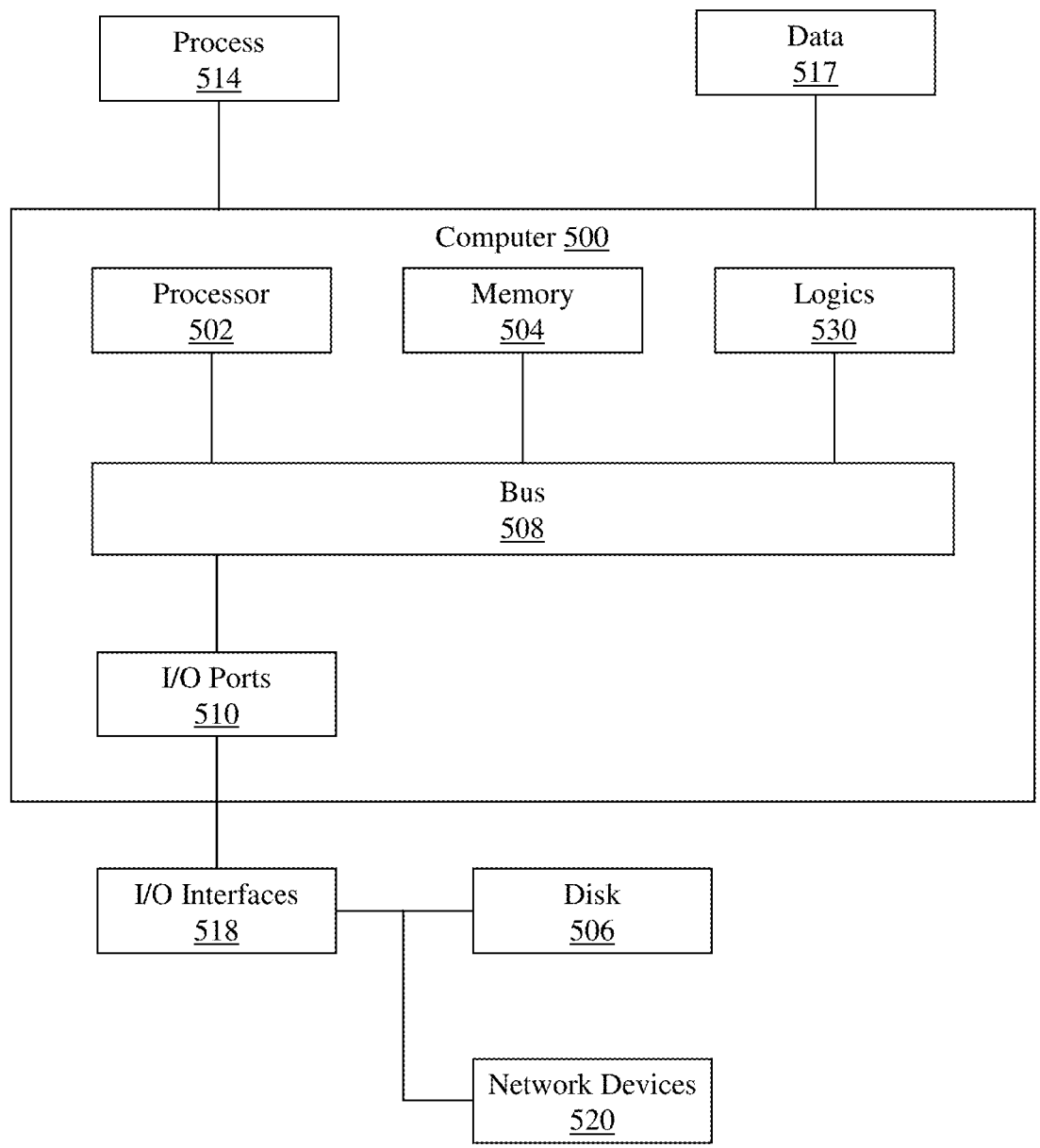
FIG. 5 illustrates an example computer in which example methods and apparatus described herein operate.

FIG. 5 illustrates an example computer 500 in which example methods illustrated herein can operate and in which example circuits and apparatus may be implemented. In different examples, computer 500 may be part of a CT system or an MRI system, may be operably connectable to a CT system or an MRI system, or may be part of a CADx system.

Computer 500 includes a processor 502, a memory 504, and input/output ports 510 operably connected by a bus 508. In one example, computer 500 may include a set of logics 530 that perform a method of distinguishing IA from AIS in a region of tissue demonstrating cancerous pathology. Thus, the set of logics 530, whether implemented in computer 500 as hardware, firmware, and/or a combination thereof may provide means (e.g., circuits, hardware) for distinguishing IA from AIS in a region of tissue demonstrating cancerous pathology. In different examples, the set of logics 530 may be permanently and/or removably attached to computer 500. In one embodiment, the functionality associated with the set of logics 530 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 530 are implemented as ASICs or SOCs.

Processor 502 can be a variety of various processors including dual microprocessor and other multi-processor architectures. Memory 504 can include volatile memory and/or non-volatile memory. A disk 506 may be operably connected to computer 500 via, for example, an input/output interface (e.g., card, device) 518 and an input/output port 510. Disk 506 may include, but is not limited to, devices like a magnetic disk drive, a tape drive, a Zip drive, a flash memory card, or a memory stick. Furthermore, disk 506 may include optical drives like a CD-ROM or a digital video ROM drive (DVD ROM). Memory 504 can store processes 514 or data 517, for example. Disk 506 or memory 504 can store an operating system that controls and allocates resources of computer 500.

Bus 508 can be a single internal bus interconnect architecture or other bus or mesh architectures. While a single bus is illustrated, it is to be appreciated that computer 500 may communicate with various devices, logics, and peripherals using other busses that are not illustrated (e.g., PCIE, SATA, Infiniband, 1394, USB, Ethernet).

Computer 500 may interact with input/output devices via I/O interfaces 518 and input/output ports 510. Input/output devices can include, but are not limited to, digital whole slide scanners, an optical microscope, a keyboard, a microphone, a pointing and selection device, cameras, video cards, displays, disk 506, network devices 520, or other devices. Input/output ports 510 can include but are not limited to, serial ports, parallel ports, or USB ports.

Computer 500 may operate in a network environment and thus may be connected to network devices 520 via I/O interfaces 518 or I/O ports 510. Through the network devices 520, computer 500 may interact with a network. Through the network, computer 500 may be logically connected to remote computers. The networks with which computer 500 may interact include, but are not limited to, a local area network (LAN), a wide area network (WAN), or other networks.

One example method for distinguishing invasive adenocarcinoma (IA) from non-invasive adenocarcinoma (AIS) includes accessing a computed tomography (CT) image of a region of tissue demonstrating cancerous pathology; extracting a set of texture features from the CT image; providing the set of texture features to an automated IA classifier, where the IA classifier is trained on a set of composite images, where the composite images are formed from a set of three dimensional (3D) histology reconstructions of a region of tissue demonstrating IA or AIS combined with a set of 3D CT images of the region of tissue demonstrating IA or IAS, where combining the set of 3D histology reconstructions with the set of 3D CT images includes: accessing a set of histology slices of a region of tissue demonstrating cancerous pathology, where a member of the set of histology slices includes an invasive component and a non-invasive component, and where a member of the set of histology slices has a thickness; generating a 3D histology reconstruction of the set of histology slices using an iterative group-wise registration of at least two members of the set of histology slices, where the 3D histology reconstruction has a slice spacing that is less than the slice thickness; accessing a set of 3D radiological images of the region of tissue, where a member of the set of 3D radiological images includes a texture feature or a shape feature; identifying an optimal translation of the set of 3D radiological images relative to the 3D histology reconstruction; identifying an optimal rotation of the set of 3D radiological images relative to the 3D histology reconstruction using a global search that includes a grid-like search to achieve alignment between the set of 3D radiological images and the 3D histology reconstruction, where the grid-like search is based on an intensity-based medical image registration approach, or on a full search space optimization; registering the 3D histology reconstruction with the set of 3D radiological images based, at least in part, on the optimal translation or the optimal rotation; mapping the extent of cancerous invasion from the 3D histology reconstruction onto the set of 3D radiological images; and identifying, based, at least in part on the mapping, a texture feature or a shape feature associated with an invasive component; receiving, from the IA classifier, a classification of the set of texture features; and classifying the region of tissue as IA or AIS, based, at least in part, on the set of texture features and the classification.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic device, an application specific integrated circuit (ASIC), a compact disk (CD), other optical device, a random access memory (RAM), a read only memory (ROM), a memory chip or card, a memory stick, and other media or device from which a computer, a processor or other electronic device can read.

"Circuit", as used herein, includes but is not limited to hardware, or firmware, or combinations of each to perform a function(s) or an action(s), or to cause a function or action from another circuit, logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple circuits are described, it may be possible to incorporate the multiple circuits into one circuit. Similarly, where a single circuit is described, it may be possible to distribute that single circuit between multiple circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method for distinguishing invasive cancerous pathology from non-invasive pathology, the method comprising:
    accessing a set of histology slices of a region of tissue demonstrating invasive cancerous pathology and non-invasive cancerous pathology, where a member of the set of histology slices has a thickness;
    generating a three dimensional (3D) histology reconstruction of the set of histology slices;
    accessing a set of 3D radiological images of the region of tissue, where a member of the set of 3D radiological images includes a texture feature or a shape feature;
    registering the 3D histology reconstruction with the set of 3D radiological images;
    generating a mapping of invasive cancerous pathology from the 3D histology reconstruction onto the set of 3D radiological images based, at least in part, on the registration;
    identifying, in a member of the set of 3D radiological images, a texture feature or a shape feature associated with invasive cancerous pathology based, at least in part, on the mapping; and
    training a classifier to distinguish invasive cancerous pathology from non-invasive cancerous pathology based, at least in part, on the mapping.

2. The method of claim 1, further comprising:
accessing a diagnostic 3D radiological image of a region of tissue demonstrating cancerous pathology;
extracting a texture feature or a shape feature from the diagnostic 3D radiological image;
providing the extracted texture feature or the extracted shape feature to the classifier;
receiving, from the classifier, a first classification; and
distinguishing invasive cancerous pathology represented in the diagnostic 3D radiological image from non-invasive cancerous pathology represented in the diagnostic 3D image based, at least in part, on the first classification and the texture feature or the shape feature.

3. The method of claim 1, where the set of histology slices is preprocessed by down-sampling a member of the set of histology slices.

4. The method of claim 3, where the member of the set of histology slices is down-sampled to a pixel resolution of 39 μm in the X-Y plane.

5. The method of claim 1, where the set of histology slices is preprocessed by rotating a first member of the set of histology slices to within a threshold level of gross alignment relative to at least one other different member of the set of histology slices.

6. The method of claim 1, where generating the 3D histology reconstruction of the set of histology slices comprises:
performing a group-wise registration of at least two members of the set of histology slices.

7. The method of claim 6, where performing the group-wise registration includes aligning the at least two members of the set of histology slices using a rigid transformation.

8. The method of claim 7, where the rigid transformation includes an in-plane 2D translation or a rotation.

9. The method of claim 6, where performing the group-wise registration comprises:
iteratively registering a first member of the set of histology slices relative to a second, different member of the set of histology slices; and
iteratively registering at least a third, different member of the set of histology slices relative to the first and second members of the set of histology slices.

10. The method of claim 9, where iteratively registering the first member of the set of histology slices relative to the second, different member of the set of histology slices is based on a first mutual information associated with the first member of the set of histology and the second, different member of the set of histology slices, where the first mutual information is used to assess a spatial alignment between the first member of the set of histology slices and the second, different member of the set of histology slices.

11. The method of claim 10, where iteratively registering the at least a third, different member is based, at least in part, on a weighted average of the first mutual information and a second different mutual information associated with the at least a third, different member.

12. The method of claim 1, generating the 3D histology reconstruction includes using a slice spacing that is less than the slice thickness.

13. The method of claim 12, where the slice thickness is 5 mm, and where generating the 3D histology reconstruction includes using a slice spacing of 3 mm.

14. The method of claim 12, where the slice thickness is 5 mm, and where generating the 3D histology reconstruction includes using a slice spacing of 4 mm.

15. The method of claim 12, where the slice thickness is 5 mm, and where generating the 3D histology reconstruction includes using a slice spacing of between 3 mm and 4 mm.

16. The method of claim 1 where registering the 3D histology reconstruction with the set of 3D radiological images comprises:
identifying an optimal rotation of the set of 3D radiological images relative to the 3D histology reconstruction using a global search.

17. The method of claim 16, where the global search includes a grid-like search to achieve alignment between the set of 3D radiological images and the 3D histology reconstruction, where the grid-like search is based on an intensity-based medical image registration approach, or on a full search space optimization.

18. An apparatus, comprising:
a processor;
a memory;
a data store that stores a set of three dimensional (3D) radiological images of tissue demonstrating invasive adenocarcinoma (IA) or non-invasive adenocarcinoma (AIS), where a member of the set of 3D radiological images includes a texture feature or a shape feature;
an input/output interface;
a set of circuits; and
an interface to connect the processor, the memory, the data store, the input/output interface and the set of circuits, where the set of circuits includes:
a classification circuit that generates an invasiveness classification for a diagnostic 3D radiological image;
a training circuit that trains the classification circuit to identify a texture feature or a shape feature associated with IA or AIS;
an image acquisition circuit that accesses a diagnostic 3D radiological image of a region of tissue demonstrating cancerous pathology and that provides the diagnostic 3D radiological image to the classification circuit, where the diagnostic 3D radiological image includes a texture feature or a shape feature; and
an IA prediction circuit that generates an invasiveness score based, at least in part, on the diagnostic 3D radiological image and the invasiveness classification.

19. The apparatus of claim 18, where the classification circuit generates the invasiveness classification by distinguishing IA from AIS represented in the diagnostic 3D radiological image based, at least in part, on a texture feature extracted from the diagnostic 3D radiological image or a shape feature extracted from the diagnostic 3D radiological image.

20. The apparatus of claim 18, where the training circuit trains the classification circuit using a 3D histology reconstruction of a region of tissue demonstrating IA or AIS combined with the set of 3D radiological images of the region of tissue.

21. The apparatus of claim 20, where the training circuit combines the 3D histology reconstruction with the set of 3D radiological images by accessing a set of histology slices of a region of tissue demonstrating IA or AIS, where a member of the set of histology slices has a thickness, generating a 3D histology reconstruction of the set of histology slices, accessing the set of 3D radiological images of the region of tissue, registering the 3D histology reconstruction with the set of 3D radiological images, generating a mapping of IA from the 3D histology reconstruction onto the set of 3D radiological images, and identifying, in a member of the set of 3D radiological images, a texture feature or a shape feature associated with IA based, at least in part, on the mapping.

22. The apparatus of claim 21, where generating a 3D histology reconstruction of the set of histology slices includes iteratively registering a first member of the set of histology slices relative to a second, different member of the set of histology slices; and iteratively registering at least a third, different member of the set of histology slices relative to the first and second members of the set of histology slices.

23. The apparatus of claim 21, where registering the 3D histology reconstruction with the set of 3D radiological images includes:
    identifying an optimal translation of the set of 3D radiological images relative to the 3D histology reconstruction;
    identifying an optimal rotation of the set of 3D radiological images relative to the 3D histology reconstruction; and
    registering the 3D histology reconstruction with the set of 3D radiological images based, at least in part, on the optimal rotation and the optimal translation,
    where identifying the optimal rotation includes using a grid-like search to achieve alignment between the set of 3D radiological images and the 3D histology reconstruction, where the grid-like search is based on an intensity-based medical image registration approach, or on a full search space optimization.

24. The apparatus of claim 21, comprising a display circuit that controls a computer assisted diagnostic (CADx) system to display the invasiveness classification, the diagnostic 3D radiological image, the texture feature, the shape feature, or the 3D histology reconstruction combined with the set of 3D radiological images.

25. The apparatus of claim 21, where the training circuit generates the 3D histology reconstruction of the set of histology slices using a slice spacing that is less than the slice thickness.

26. A non-transitory computer-readable storage device storing computer executable instructions that when executed by a computer control the computer to perform a method for distinguishing invasive adenocarcinoma (IA) from non-invasive adenocarcinoma (AIS), the method comprising:
    accessing a computed tomography (CT) image of a region of tissue demonstrating cancerous pathology;
    extracting a set of texture features from the CT image;
    providing the set of texture features to an automated IA classifier, where the IA classifier is trained on a set of composite images, where the composite images are formed from a set of three dimensional (3D) histology reconstructions of a region of tissue demonstrating IA or AIS combined with a set of 3D CT images of the region of tissue demonstrating IA or IAS, where combining the set of 3D histology reconstructions with the set of 3D CT images includes:
        accessing a set of histology slices of a region of tissue demonstrating cancerous pathology, where a member of the set of histology slices includes an invasive component and a non-invasive component, and where a member of the set of histology slices has a thickness;
        generating a 3D histology reconstruction of the set of histology slices using an iterative group-wise registration of at least two members of the set of histology slices, where the 3D histology reconstruction has a slice spacing that is less than the slice thickness;
        accessing a set of 3D radiological images of the region of tissue, where a member of the set of 3D radiological images includes a texture feature or a shape feature;
        identifying an optimal translation of the set of 3D radiological images relative to the 3D histology reconstruction;
        identifying an optimal rotation of the set of 3D radiological images relative to the 3D histology reconstruction using a global search that includes a grid-like search to achieve alignment between the set of 3D radiological images and the 3D histology reconstruction, where the grid-like search is based on an intensity-based medical image registration approach, or on a full search space optimization;
        registering the 3D histology reconstruction with the set of 3D radiological images based, at least in part, on the optimal translation or the optimal rotation;
        mapping the extent of cancerous invasion from the 3D histology reconstruction onto the set of 3D radiological images; and
        identifying, based, at least in part on the mapping, a texture feature or a shape feature associated with an invasive component;
    receiving, from the IA classifier, a classification of the set of texture features; and
    classifying the region of tissue as IA or AIS, based, at least in part, on the set of texture features and the classification.

* * * * *